(12) United States Patent
Flaugh

(10) Patent No.: US 6,221,884 B1
(45) Date of Patent: *Apr. 24, 2001

(54) CARBOXAMIDES USEFUL AS 5-HT$_{1F}$ AGONISTS

(75) Inventor: Michael Edward Flaugh, Indianapolis, IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/486,652

(22) PCT Filed: Jun. 1, 1998

(86) PCT No.: PCT/US98/03340

§ 371 Date: Dec. 21, 1999

§ 102(e) Date: Dec. 21, 1999

(87) PCT Pub. No.: WO98/55115

PCT Pub. Date: Dec. 10, 1998

Related U.S. Application Data

(60) Provisional application No. 60/048,584, filed on Jun. 4, 1997.

(51) Int. Cl.[7] .................. A61K 31/403; A61K 31/4439; C07D 209/88; C07D 401/12
(52) U.S. Cl. ........................ 514/339; 514/411; 546/276.7; 548/448
(58) Field of Search ........................ 548/448; 546/276.7; 514/339, 411

(56) References Cited

U.S. PATENT DOCUMENTS

| 5,708,008 | 1/1998 | Audia et al. | 514/323 |
| 5,708,187 | 1/1998 | Flaugh et al. | 548/439 |

FOREIGN PATENT DOCUMENTS

94/14773   7/1994   (WO) .

*Primary Examiner*—Laura L. Stockton
(74) *Attorney, Agent, or Firm*—Robert D. Titus

(57) ABSTRACT

The present invention provides novel 2-amino-1,2,3,4-tetrahydro-9H-carbazole-6-carboxamides and 3-amino-10H-cyclohepta[7,6-b]indole-7-carboxamides of Formula I:

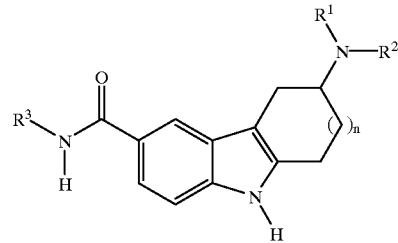

where $R^1$, $R^2$, $R^3$ and n are as described in the specification.

12 Claims, No Drawings

CARBOXAMIDES USEFUL AS 5-HT$_{1F}$ AGONISTS

This is a 371 of PCT/US98/03340 filed Jun. 1, 1998 which claims the benefit of Provisional Application Ser. No. 60/048,584 filed Jun. 4, 1997.

Theories regarding the pathophysiology of migraine have been dominated since 1938 by the work of Graham and Wolff (*Arch. Neurol. Psychiatry*, 39, 737–63 (1938)). They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. (Humphrey, et al., *Ann. NY Acad. Sci.*, 600, 587–600 (1990)). Recent work by Moskowitz has shown, however, that the occurrence of migraine headaches is independent of changes in vessel diameter (*Cephalalgia*, 12, 5–7, (1992)).

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers (*Neurology*, 43(suppl. 3), S16–S20 (1993)).

Serotonin (5-HT) exhibits diverse physiological activity mediated by at least four receptor classes, the most heterogeneous of which appears to be 5-HT$_1$. A human gene which expresses a fifth 5-HT$_1$ subtype, named 5-HT$_{1F}$, was isolated by Kao and coworkers (*Proc. Natl. Acad. Sci. USA*, 90, 408–412 (1993)). This 5-HT$_{1F}$ receptor exhibits a pharmacological profile distinct from any serotonergic receptor yet described. The high affinity of sumatriptan at this subtype, $K_i$=23 nM, suggests a role of the 5-HT$_{1F}$ receptor in migraine.

A series of N-aryl-3-amino-1,2,3,4-tetrahydro-9H-carbazole-6-carboxamides have been described by Porter, et al., (WO 94/14773, Jul. 7, 1994) as 5-HT$_1$-like agonists, which exhibited vasoactive effects. The amides of the present invention are 5-HT$_{1F}$ agonists which inhibit peptide extravasation due to stimulation of the trigeminal ganglia, and are therefore useful for the treatment of migraine and associated disorders without the vasoconstrictive liability of structurally similar compounds.

The present invention provides novel 3-amino-1,2,3,4-tetrahydro-9H-carbazole-6-carboxamides and 4-amino-10H-cyclohepta[7,6-b]indole-7-carboxamides of Formula I:

I

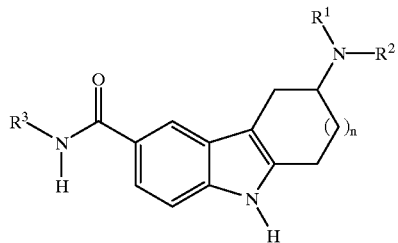

wherein:

R$^1$ and R$^2$ are independently hydrogen, C$_1$–C$_4$ alkyl, or —CH$_2$CH$_2$-Aryl where Aryl is phenyl, phenyl monosubstituted with halo, or 1-(C$_1$–C$_6$ alkyl)pyrazol-4-yl;

R$^3$ is C$_3$–C$_6$ cycloalkyl, or a heterocycle;

n is 1 or 2; and pharmaceutically acceptable salts and hydrates thereof.

A further embodiment of this invention is a method for increasing activation of the 5-HT$_{1F}$ receptor by administering a compound of Formula I.

A further embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, dysphoric disorder, alcoholism, tobacco abuse, panic disorder, anxiety, general pain, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, trichotillomania, trigeminal neuralgia, dental pain or temperomandibular joint dysfunction pain. The compounds of this invention are also useful as a prophylactic treatment for migraine. Any of these methods employ a compound of Formula I.

In addition, this invention provides pharmaceutical formulations comprising an effective amount for activation of the 5-HT$_{1F}$ receptor of a compound of Formula I, in combination with a suitable pharmaceutical carrier, diluent, or excipient.

The general chemical terms used in the formulae above have their usual meanings. For example, the term "alkyl" includes such groups as methyl, ethyl, n-propyl, isopropyl, n-butyl, isobutyl, sec-butyl, tert-butyl, and the like. The term "cycloalkyl" includes cyclopropyl, cyclobutyl, cyclopentyl, and cyclohexyl. The term "alkoxy" includes such groups as methoxy, ethoxy, isopropoxy, tert-butoxy, and the like. The term "halo" includes fluoro, chloro, bromo, and iodo.

The term "heterocycle" is taken to mean fur-2-yl, fur-3-yl, thien-2-yl, thien-3-yl, pyridin-3-yl, pyridin-4-yl, pyrrol-3-yl, N-methylpyrrol-3-yl, oxazol-5-yl, isoxazol-4-yl, isoxazol-5-yl, pyrazol-4-yl, pyrimidin-5-yl, or pyrazin-4-yl. These heterocycles contain unsubstituted carbon atoms. Up to three available carbon atoms within any heterocyclic system may optionally be substituted with substituents independently selected from the group consisting of halo, C$_1$–C$_4$ alkyl, C$_1$–C$_4$ alkoxy, or C$_1$–C$_4$ alkoxycarbonyl.

The compounds of the present invention possess an asymmetric carbon. This carbon is labelled with an asterisk in the following formula:

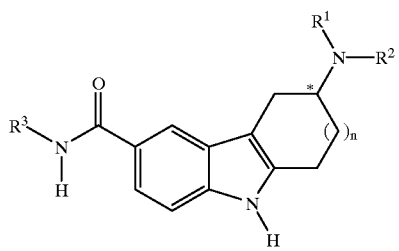

As such, each of the compounds of the present invention exists not only as the racemate but as individual R- and S-enantiomers as well:

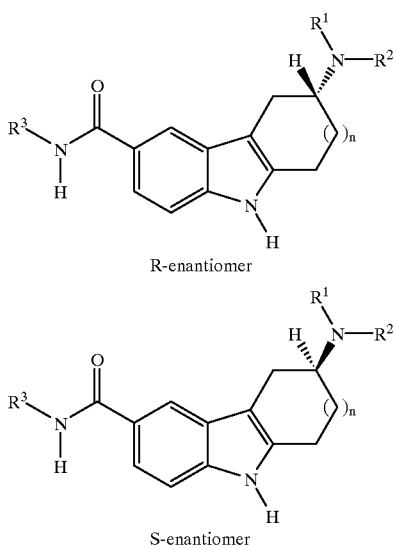

R-enantiomer

S-enantiomer

The compounds of the present invention include not only the racemates, but also their respective optically active R- and S-enantiomers and any mixture thereof. While all racemates, mixtures, and individual enantiomers are useful 5-$HT_{1F}$ agonists, it is preferred that the compound exist as a single enantiomer.

While all of the compounds of this invention are useful as 5-$HT_{1F}$ agonists, certain classes are preferred. The following paragraphs describe such preferred classes.

aa) $R^1$ is hydrogen;
ab) $R^1$ is $C_1$–$C_6$ alkyl;
ac) $R^1$ is ethyl;
ad) $R^1$ is methyl;
ae) $R^1$ is —$CH_2CH_2$-Ar where Ar is 1-($C_1$–$C_6$ alkyl)-pyrazol-4-yl;
af) $R^1$ is —$CH_2CH_2$-Ar where Ar is 1-methylpyrazol-4-yl;
ag) $R^1$ is —$CH_2CH_2$-Ar where Ar is 1-isopropylpyrazol-4-yl;
ah) $R^2$ is hydrogen;
ai) $R^2$ is $C_1$–$C_6$ alkyl;
aj) $R^2$ is ethyl;
ak) $R^2$ is methyl;
al) $R^2$ is —$CH_2CH_2$-Ar where Ar is 1-($C_1$–$C_6$ alkyl)-pyrazol-4-yl;
am) $R^2$ is —$CH_2CH_2$-Ar where Ar is 1-methylpyrazol-4-yl;
an) $R^2$ is —$CH_2CH_2$-Ar where Ar is 1-isopropylpyrazol-4-yl;
ao) $R^3$ is a heterocycle;
ap) $R^3$ is pyridin-3-yl;
aq) $R^3$ is pyridin-4-yl;
ar) $R^3$ is pyridin-3-yl or pyridin-4-yl monosubstituted with halo;
as) $R^3$ is pyridin-3-yl or pyridin-4-yl monosubstituted with chloro;
at) $R^3$ is pyridin-3-yl or pyridin-4-yl monosubstituted with fluoro;
au) $R^3$ is fur-2-yl or fur-3-yl;
av) $R^3$ is thien-2-yl or thien-3-yl;
aw) $R^3$ is pyrrol-3-yl;
ax) $R^3$ is oxazol-5-yl;
ay) $R^3$ is isoxazol-4-yl or isoxazol-5-yl;
az) $R^3$ is pyrazol-4-yl;
ba) $R^3$ is pyrimidin-5-yl;
bb) $R^3$ is pyrazin-4-yl;
bc) $R^3$ is fur-2-yl or fur-3-yl optionally substituted with $C_1$–$C_4$ alkyl, $C_1$–$C_4$ alkoxy, or halo;
bd) $R^3$ is fur-2-yl;
be) $R^3$ is fur-3-yl;
bf) $R^3$ is thien-2-yl or thien-3-yl optionally substituted with $C_1$–$C_4$ alkyl or $C_1$–$C_4$ alkoxy;
bg) $R^3$ is thien-2-yl;
bh) $R^3$ is thien-3-yl;
bi) $R^3$ is pyridin-3-yl or pyridin-4-yl optionally substituted with halo, $C_1$–$C_4$ alkyl or $C_1$–$C_4$ alkoxy;
bj) $R^3$ is 6-halopyridin-3-yl;
bk) $R^3$ is $C_3$–$C_6$ cycloalkyl;
bl) $R^3$ is cyclopropyl;
bm) n is 1;
bn) n is 2;
bo) The compound is a racemate;
bp) The compound is the R-enantiomer;
bq) The compound is the S-enantiomer;
br) The compound is a free base;
bs) The compound is a salt;
bt) The compound is the hydrochloride salt;
bu) The compound is the fumarate salt;
bv) The compound is the oxalate salt.

It will be understood that the above classes may be combined to form additional preferred classes.

The compounds of this invention are useful in a method for increasing activation of the 5-$HT_{1F}$ receptor for treating a variety of disorders which have been linked to decreased neurotransmission of serotonin in mammals. It is preferred that the mammal to be treated by the administration of compounds of this invention is human.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, b-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, oxalic acid or fumaric acid.

The following group is illustrative of compounds contemplated within the scope of this invention:

N-(4-methylthien-2-yl)-3-(propyl)amino-1,2,2,4-tetrahydro-9H-carbazole-6-carboxamide hydrochloride (+)-N-(thien-3-yl)-3-(dimethyl)amino-1,2,3,4-tetrahydro-9H-carbazole-6-carboxamide sulfate N-(4-chlorofur-2-yl)-3-(propyl)amino-1,2,3,4-tetrahydro-9H-carbazole-6-carboxamide N-(fur-3-yl)-3-(diethyl)amino-1,2,3,4-tetrahydro-9H-carbazole-6-carboxamide N-(pyridin-3-yl)-3-(diethyl)amino-1,2,3,4-tetrahydro-9H-carbazole-6-carboxamide phosphate N-(3-chloropyridin-4-yl)-3-(diethyl)amino-1,2,3,4-tetrahydro-9H-carbazole-6-carboxamide N-(oxazol-5-yl)-3-(propyl)amino-1,2,3,4-tetrahydro-9H-carbazole-6-carboxamide p-toluenesulfonate (+)-N-(isoxazol-4-yl)-3-(dimethyl)amino-1,2,3,4-tetrahydro-9H-carbazole-6-carboxamide N-(pyrazol-4-yl)-3-(propyl)amino-1,2,3,4-tetrahydro-9H-carbazole-6-carboxamide methanesulfonate N-(cyclobutyl)-3-(diethyl)amino-1,2,3,4-tetrahydro-9H-carbazole-6-carboxamide oxalate N-(cyclohexyl)-3-(propyl)amino-1,2,3,4-tetrahydro-9H-carbazole-6-carboxamide (+)-N-(2-methylpyrimidin-5-yl)-3-(dimethyl)amino-1,2,3,4-tetrahydro-9H-carbazole-6-carboxamide formate (−)-N-(thien-2-yl)-4-(methyl)amino-10H-cyclohepta[7,6-b]indole-7-carboxamide N-(thien-3-yl)-4-(dimethyl)amino-10H-cyclohepta[7,6-b]indole-7-carboxamide butyne-1,4-dioate N-(fur-2-yl)-4-(propyl)amino-10H-cyclohepta[7,6-b]indole-7-carboxamide N-(fur-3-yl)-4-(diethyl)amino-10H-cyclohepta[7,6-b]-indole-7-carboxamide trifluoroacetate N-(pyridin-3-yl)-4-(diisopropyl)amino-10H-cyclohepta-[7,6-b]indole-7-carboxamide N-(3-chloropyridin-4-yl)-4-(dibutyl)amino-10H-cyclohepta[7,6-b]indole-7-carboxamide (−)-N-(pyrrol-3-yl)-4-(methyl)amino-10H-cyclohepta[7,6-b]indole-7-carboxamide tartrate N-(2-isopropyloxazol-5-yl)-4-(dimethyl)amino-10H-cyclohepta[7,6-b]indole-7-carboxamide N-(3-bromo-4-methylisoxazol-5-yl)-4-(propyl)amino-10H-cyclohepta[7,6-b]indole-7-carboxamide cinnamate N-(3-ethylpyrazol-4-yl)-4-(diethyl)amino-10H-cyclohepta[7,6-b]indole-7-carboxamide N-(cyclopropyl)-4-(diisopropyl)amino-10H-cyclohepta-[7,6-b]indole-7-carboxamide N-(cyclohexyl)-4-(dibutyl)amino-10H-cyclohepta[7,6-b]indole-7-carboxamide mandelate (−)-N-(2-methoxypyrimidin-5-yl)-4-(methyl)amino-10H-cyclohepta[7,6-b]indole-7-carboxamide N-(2-fluoropyrazin-4-yl)-4-(dimethyl)amino-10H-cyclohepta[7,6-b]indole-7-carboxamide N-(cyclobutyl)-4-(propyl)amino-10H-cyclohepta[7,6-b]indole-7-carboxamide N-(cyclopentyl)-4-(diethyl)amino-10H-cyclohepta[7,6-b]indole-7-carboxamide 4-methoxybenzoate N-(cyclohexyl)-4-(diisopropyl)amino-10H-cyclohepta[7,6-b]indole-7-carboxamide The compounds of this invention are prepared by methods well known to one of ordinary skill in the art. Compounds of the present invention where n is 1 are members of the class commonly known as 3-amino-1,2,3,4-tetrahydro-9H-carbazole-6-carboxamides. Members of this class are conveniently prepared by the Fischer indole synthesis as described in Synthetic Scheme I where $R^{1'}$ and $R^{2'}$ are independently $C_1$–$C_6$ alkyl, benzyl or, together with the nitrogen to which they are attached, form a phthalimido group, and $R^3$ is as previously defined.

Synthetic Scheme I

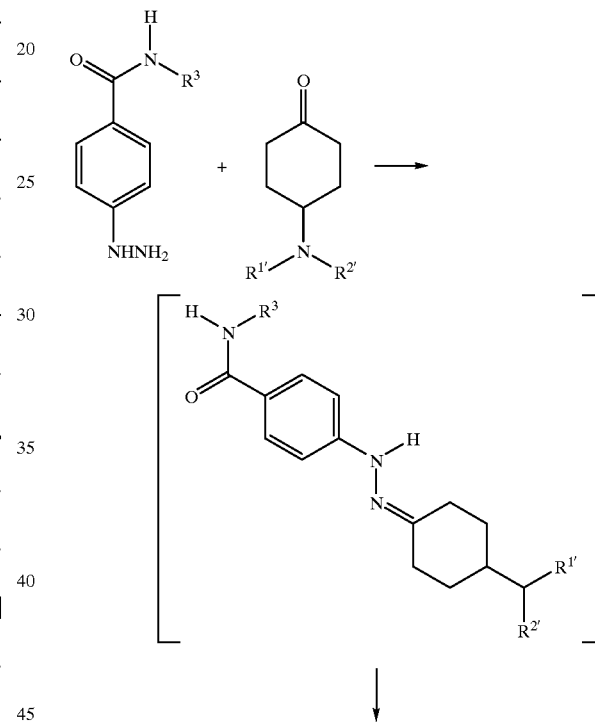

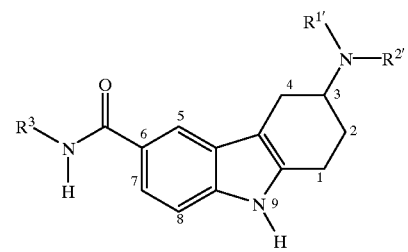

The phenylhydrazine and 4-aminocyclohexanone are condensed together in a suitable solvent, typically a lower alkanol such as ethanol, in the presence of a catalytic amount of acid, such as hydrogen chloride, to give the resultant phenylhydrazone. The reaction is typically performed at from about room temperature to reflux for from about 1 to 24 hours. Once the condensation is complete, the resulting phenylhydrazone may be isolated from the reaction mixture by the addition of water or an aqueous solution of a base such as potassium carbonate if desired. The product separates from the mixture as an oil or a solid. The product may be extracted with a water immiscible solvent, typically dichloromethane, or filtered if appropriate. The product may be used in the next step with or without further purification. The phenylhydrazone undergoes a Fischer indole cyclization in the presence of excess acid. This may be accomplished by dissolving the phenylhydrazone in a neat acid, for example, acetic acid. Alternatively, the phenyl hydrazone may be dissolved in a lower alkanol which has been treated with an acid, for example, ethanolic hydrogen chloride. If the phenylhydrazone prepared as described above requires no further purification, the original reaction mixture may conveniently be treated with an appropriate acid without isolation of the phenylhydrazone. Many times, the Fischer indole cyclization occurs upon formation of the phenylhydrazone, giving the desired product in one step. The reaction is performed at from about room temperature to reflux for from about 1 to 24 hours. The reaction product may be recovered by direct filtration, or by extraction after removal of solvent and neutralization of acid by the addition of aqueous base. The product may be purified by recrystallization or chromatography as required. While Synthetic Scheme I describes the use of an amidophenylhydrazine, the skilled artisan will appreciate that the Fischer indolization may also be performed on the corresponding carboxylic acid or ester. The amide moiety may then be introduced later in the synthesis as necessary or desired.

The phenylhydrazines required for the preparation of compounds of the invention are either commercially available or may be prepared by methods well known to those skilled in the art from 4-nitrobenzoic acid as described in Synthetic Scheme II. $R^3$ is as previously defined.

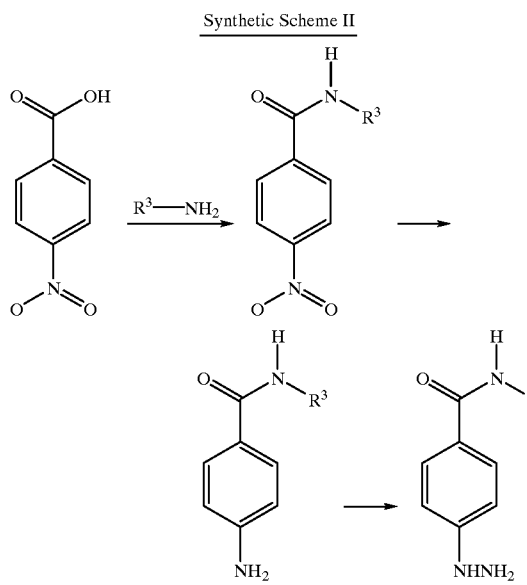

Synthetic Scheme II

The carboxylic acid may first be converted to the corresponding acid chloride or bromide under standard conditions such as treatment with thionyl chloride or bromide. The corresponding acid halide, optionally in the presence of an acylation catalyst such as dimethylaminopyridine, is reacted with an appropriate amine of formula $R^3$—$NH_2$, in the presence of a suitable base. Suitable bases include amines typically used as acid scavengers, such as pyridine or triethylamine, or commercially available polymer bound bases such as polyvinylpyridine. Alternatively, the requisite amine is reacted with an appropriate carboxylic acid in the presence of typical peptide coupling reagents such as N,N'- carbonyldiimidazole (CDI), N,N'-dicyclohexylcarbodiimide (DCC) and 1-(3-dimethylaminopropyl)-3-ethylcarbodiimide hydrochloride (EDC). A polymer supported form of EDC has been described (*Tetrahedron Letters*, 34(48), 7685 (1993)) and is very useful for the preparation of the compounds of the present invention. The product from these reactions is isolated by standard extractive techniques and purified by standard chromatographic and crystallization techniques as necessary or desired to provide the compounds of the present invention. Isolation of products from reactions where a polymer bound reagent has been used is greatly simplified, requiring only filtration of the reaction mixture and then concentration of the filtrate under reduced pressure. The product from these reactions may then be purified as described supra.

The nitrocarboxamides are hydrogenated over a precious metal catalyst, preferably platinum on carbon, at about ambient temperature with an initial pressure of about 60 p.s.i. for from 1 to 24 hours in a suitable solvent, such as a lower alkanol or tetrahydrofuran, to give the corresponding aniline. This aniline is then dissolved in a concentrated acid, such as phosphoric, hydrochloric or hydrobromic acid, and treated with sodium nitrite at a temperature about or below 0° C. After stirring for about an hour, the reaction mixture is added to a solution of tin(II) chloride in concentrated hydrochloric acid and the mixture stirred at about 0° C. for about an hour. The product is isolated by treating the reaction mixture with an aqueous base until it is strongly basic and then extracting with a water immiscible solvent such as ethyl acetate. The hydrazine product may be further purified by chromatography or crystallization prior to further reaction if necessary or desired. The skilled artisan will appreciate that by substituting an appropriate alcohol for the amine in Synthetic Scheme II, esters useful for preparation of the compounds of the present invention may be prepared.

The 4-substituted cyclohexanones required for the preparation of compounds of the invention are available by methods well known in the art as illustrated in synthetic Scheme III. $R^1$ and $R^2$ independently hydrogen, $C_1$–$C_6$ alkyl or benzyl.

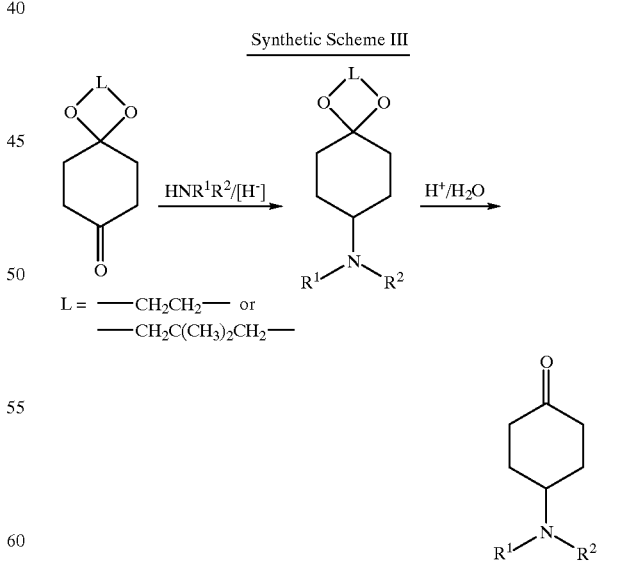

Synthetic Scheme III

The 1,4-cyclohexanedione monoketal is reductively aminated with an appropriate amine under standard conditions to give the corresponding 4-aminocyclohexanone ketal. The ketal is then deprotected under aqueous acid conditions to prepare the corresponding 4-aminocyclohexanone.

Compounds of the invention where $R^1=R^2=H$ are prepared from 4-(1-phthalimidyl)cyclohexanone which is available by methods well known in the art, for example, King et al. (*Journal of Medicinal Chemistry*, 36, 1918 (1993)). Briefly, 4-aminocyclohexanol is reacted first with N-carbethoxyphthalimide and the resulting 4-(1-phthalimidyl)cyclohexanol treated with pyridinium chlorochromate to give the desired ketone. The resultant 4-(1-phthlimidyl)cyclohexanone is then reacted with an appropriate phenylhydrazine followed by Fischer indole cyclization to prepare the corresponding 3-(1-phthalimidyl) carbazole. The phthalimide is then removed by reaction with hydrazine at a convenient point after the Fischer indole synthesis to provide compounds of the invention where $R^1=R^2=H$.

The skilled artisan will appreciate that the manipulation of the 6-substituent may occur prior to or after the cyclization described in Synthetic Scheme I. For example, the compounds of the present invention may be prepared from from the corresponding carboxylic acids, esters, acid halides, or mixed acid anhydrides as illustrated in Synthetic Scheme IV. $R^{1\prime}$ and $R^{2\prime}$ are independently $C_1-C_6$ alkyl, benzyl or, together with the nitrogen to which they are attached, form a phthalimido group; Z is hydrogen or a suitable nitrogen protecting group; Y is hydroxy, $C_1-C_6$ alkoxy, chloro, bromo, or $C_1-C_6$ alkoxycarbonyl; and $R^3$ is as previously defined.

Compounds of the invention where n=2 are 4-amino-10H-cyclohepta[6,7-b]indoles-7-carboxamides. These compounds are prepared substantially as described for the corresponding 3-amino-1,2,3,4-tetrahydro-9H-carbazole-6-carboxamides as illustrated in Synthetic Scheme I, except that a 4-aminocycloheptanone replaces the 4-aminocyclohexanone in the synthesis. The 4-aminocycloheptanones required for the synthesis of compounds of the present invention may be prepared as described in Synthetic Scheme V. $R^{1\prime}$ and $R^{2\prime}$ are independently $C_1-C_6$ alkyl or benzyl, or together with the nitrogen atom to which they are attached form the phthalimide moiety.

Synthetic Scheme V

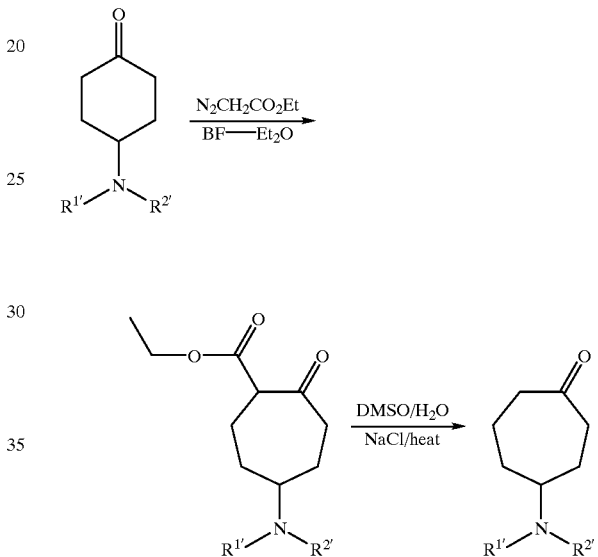

Synthetic Scheme IV

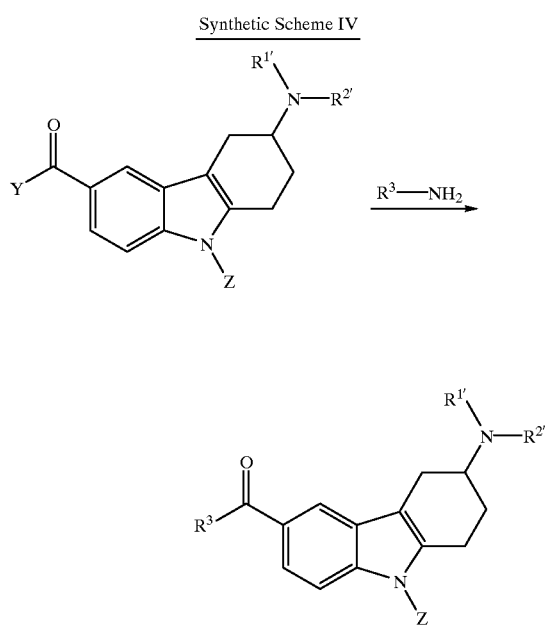

The carboxylic acid chloride, bromide, or anhydride, optionally in the presence of an acylation catalyst such as dimethylaminopyridine, is reacted with an appropriate amine of formula $R^3$—$NH_2$. Alternatively, the requisite amine is reacted with an appropriate carboxylic acid in the presence of typical peptide coupling reagents. An ester is first hydrolyzed to the carboxylic acid and then coupled with an appropriate amine. Each of these techniques are described in Synthetic Scheme II supra.

The appropriate 4-aminocyclohexanone in an appropriate solvent, for example diethyl ether, is treated with an appropriate Lewis acid such as boron trifluoride for about 20 minutes to about an hour at room temperature. To this solution is then added ethyl diazoacetate and the resulting mixture is stirred for about 1 hour to about 24 hours at room temperature. The resulting 2-ethoxycarbonyl-5-aminocycloheptanone is isolated by diluting the reaction mixture with aqueous sodium carbonate and extracting with a water immiscible solvent such as diethyl ether. The reaction product is then directly dissolved in dimethylsulfoxide which contains sodium chloride and water. The reaction mixture is heated to about 170° for from about 1 to about 24 hours to effect the decarbethoxylation. The desired 4-aminocycloheptanone is recovered by diluting the reaction mixture with water and extracting with an appropriate solvent such as diethyl ether. The reaction product may be purified by column chromatography, if desired, prior to further reaction.

After reaction with an appropriate phenylhydrazine, the corresponding 4-aminocycloheptanonephenylhydrazone is subjected to the same Fischer indole cyclization conditions as described above. The asymmetry in the cycloheptanone, however, leads to the production of the following two isomers:

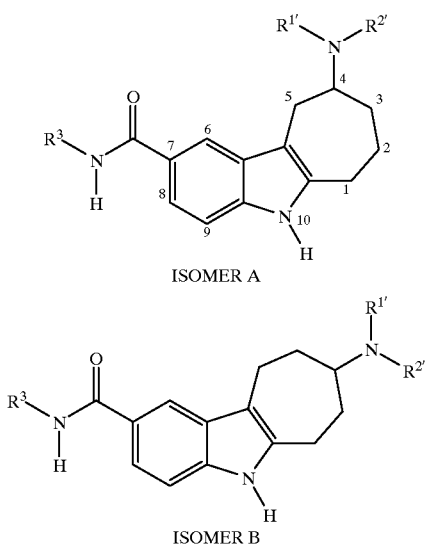

ISOMER A

ISOMER B

Isomers A and B may be separated by crystallization or chromatography at any convenient point in the synthesis of the compounds of the invention.

The intermediate carboxylic acid useful for the preparation of the compounds of the invention may either be synthesized directly from 4-carboxyphenylhydrazine by the procedures described in Synthetic Scheme I, or they be prepared from the corresponding bromo derivative. Prior to manipulation of the bromo substituent, however, the indole nitrogen must first be protected as illustrated in Synthetic Scheme VI. $R^{1''}$ and $R^{2''}$ are $C_1$–$C_6$ alkyl or benzyl.; LG is chloro, bromo, or trifluoromethanesulfonyl; and Ar is phenyl or 2,4,6-triisopropylphenyl.

A solution of the starting material in a suitable solvent, such as tetrahydrofuran or diethyl ether, is added to a suspension of an alkali metal hydride, preferably potassium hydride, in the same solvent. The deprotonation is performed at from about −10° C. to about ambient temperature for about an hour. To this solution is then added an appropriate arylsulfonyl chloride, triisopropylsilyl halide, or triisopropylsilyl triflate and the reaction is allowed to proceed for from about 1 to 24 hours. The indole nitrogen protected derivative is isolated by treating the reaction mixture with ice to decompose any unreacted hydride, diluting the reaction mixture with water, and then extracting the product with a water immiscible solvent such as dichloromethane, diethyl ether or ethyl acetate. The isolated product may be used as recovered for further reactions, or purified by crystallization or chromatography as desired. The bromo substituted substrate so protected may then be used to provide the requisite intermediate carboxylic as described in Synthetic Scheme VII. $R^{1''}$ and $R^{2''}$ are $C_1$–$C_6$ alkyl or benzyl; and Z is phenylsulfonyl, 2,4,6-triisopropylphenylsulfonyl, or triisopropylsilyl.

Synthetic Scheme VII

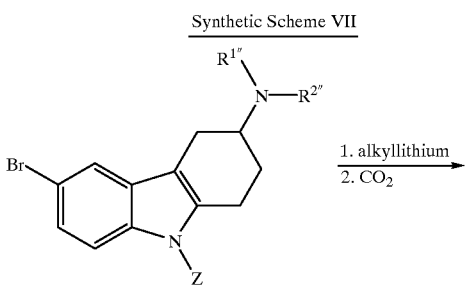

Synthetic Scheme VI

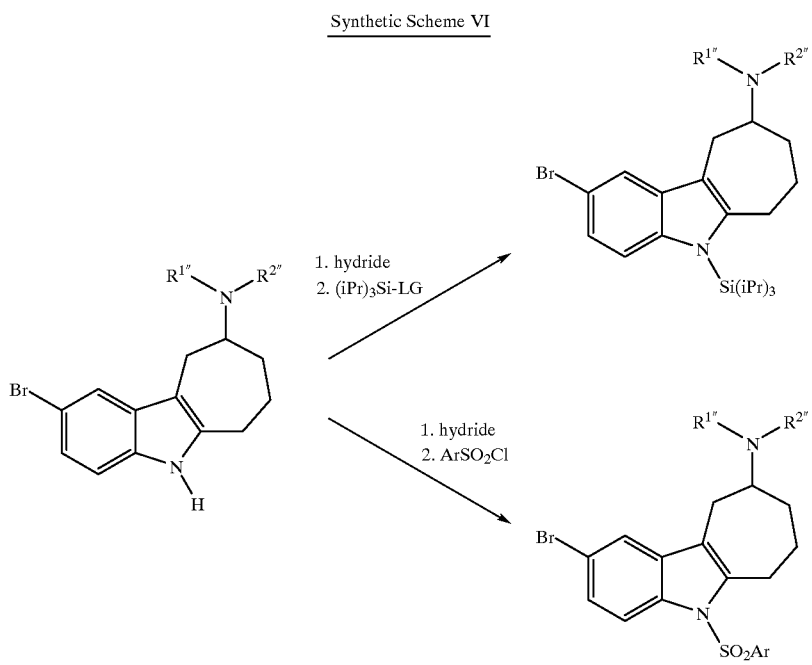

-continued

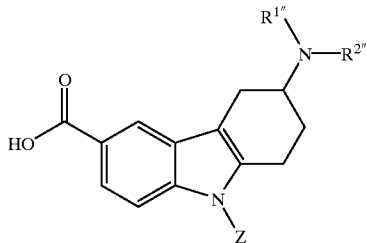

A solution of the bromo compound in an appropriate solvent, such as tetrahydrofuran or diethyl ether, is treated with an alkyllithium, such as n-butyl- or t-butyllithium, at a temperature of about −70° C. for about an hour to effect a halogen-metal exchange. The resultant anion solution is then treated with carbon dioxide at a temperature of about −70° C. The reaction mixture is then allowed to warm gradually to room temperature over from about 1 hour to about 24 hours. The resulting product is isolated by diluting the reaction mixture with aqueous ammonium chloride and extracting with a water immiscible solvent such as dichloromethane. The product may be further purified by chromatography or recrystallization as necessary.

The final step in the sequence requires deprotection of the indolic nitrogen to give the compounds of the invention as illustrated in Synthetic Scheme VIII. $R^{1\prime\prime}$, $R^{2\prime\prime}$ and Z are as previously defined.

Synthetic Scheme VIII

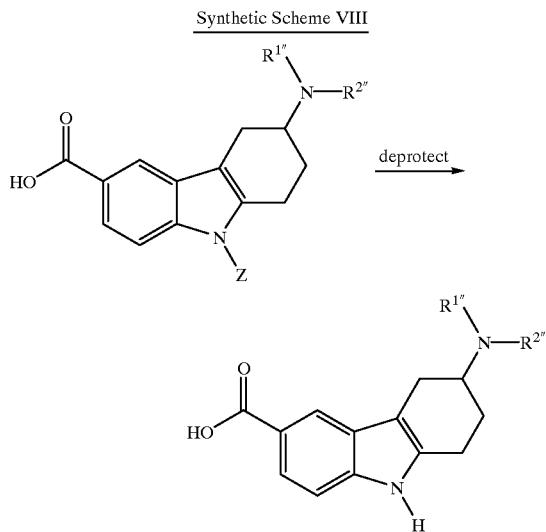

When Z is arylsulfonyl, the protecting group may be removed by basic hydrolysis in a lower alkanol such as methanol or ethanol. When Z is triisopropylsilyl, deprotection is conveniently effected by treatment with a fluoride anion reagent, preferably tetrabutylammonium fluoride, under standard conditions.

Compounds of the invention where $R^1$ and $R^2$ are independently hydrogen are available by subjecting the corresponding 3-benzylamino compounds to catalytic hydrogenation conditions over a precious metal catalyst, such as palladium or platinum on carbon, or over Raney nickel. These reactions are typically performed in a lower alkanol or tetrahydrofuran at room temperature to about 60° C., for from about 1 hour to 24 hours, at a hydrogen pressure of about 60 p.s.i. This hydrogenolysis may be performed before or after the deprotection of the indole nitrogen as desired.

Compounds where either or both of $R^1$ or $R^2$ are hydrogen may be further functionalized to prepare other compounds of the invention by reductive alkylation. Under these conditions the primary or secondary amine is reacted with an appropriate aldehyde or ketone to prepare the corresponding imine or enamine. The imine or enamine is then reduced to the desired compound by catalytic hydrogenation or by reduction with an appropriate hydride reducing reagent in the presence of an acid. Preferably, the transformation is performed by direct alkylation as illustrated in Synthetic Scheme IX. $R^{1*}$ is hydrogen or $C_1$–$C_6$ alkyl; $R^{2*}$ is $C_1$–$C_6$ alkyl or arylethyl; $X^*$ is bromo, —COOH, or $R^3NHC(O)$— and arylethyl is as previously defined.

Synthetic Scheme IX

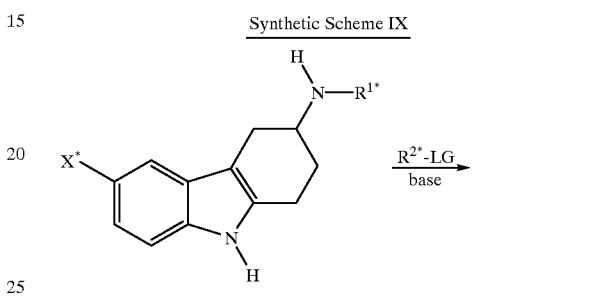

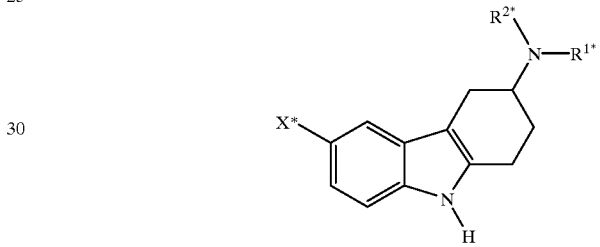

The starting amine and a base are combined in the reaction solvent followed by the addition of the alkylating agent. The reaction solvent may be any non-reactive solvent typically used for alkylations of this type such as acetonitrile, dimethylformamide or N-methyl-2-pyrrolidinone, limited by the solubility of the substrates. The base must be sufficiently basic to neutralize the acid generated during the progress of the reaction but not so basic as to deprotonate other sites in the substrate giving rise to other products. Additionally, the base must not compete to any great extent with the substrate for the alkylating agent. Bases typically used for these reactions are sodium carbonate or potassium carbonate. The reaction mixture is typically stirred at room temperature to 80° C., for about 8 hours to 3 days. The alkylated products are isolated by concentration of the reaction mixture under reduced pressure followed by partitioning of the resultant residue between water and a suitable organic solvent such as ethyl acetate, diethyl ether, dichloromethane, ethylene chloride, chloroform or carbon tetrachloride. The isolated product may be purified by chromatography, crystallization from a suitable solvent, salt formation or a combination of these techniques.

The leaving group (LG) of the alkylating agents may be chloro, bromo, iodo, methanesulfonyloxy, trifluoromethanesulfonyloxy, 2,2,2-trifluoroethanesulfonyloxy, benzenesulfonyloxy, p-bromobenzenesulfonyloxy, p-nitrobenzenesulfonyloxy or p-toluenesulfonyloxy, all of which are useful for the preparation of compounds of this invention. The specific alkylating agent employed is determined by its commercial availability or a convenient synthesis from commercially available starting materials. The preferred alkylating agents for synthesis of compounds of this invention are selected from those where the leaving group is chloro, bromo, iodo or methanesulfonyloxy. Alkylating agents where the leaving group is chloro are prepared from the corresponding alcohol by standard methods, preferably by treating the alcohol with neat thionyl chloride at ambient temperature. Alkylating agents where the leaving group is methanesulfonyloxy are prepared by treating the corresponding alcohol with a methanesulfonyl chloride or methanesulfonic anhydride. The starting alcohols required for the synthesis of compounds of this invention are either commercially available or may be prepared by employing well established synthetic methodology as described in U.S. Pat. No. 5,521,196, herein incorporated by reference in its entirety The compounds of the present invention possess a chiral center, and as such exist as racemic mixtures or individual enantiomers. As stated above, racemates and the individual enantiomers are all part of the present invention. The individual enantiomers may be resolved by fractional crystallization of salts of the racemic bases and enantiomerically pure acids, for example, ditolyltartaric acid. Alternatively, the individual enantiomers may be prepared by the use of a chiral auxiliary during the preparation of the compound as described in the following Synthetic Scheme X. X is —Br or —CO$_2$H.

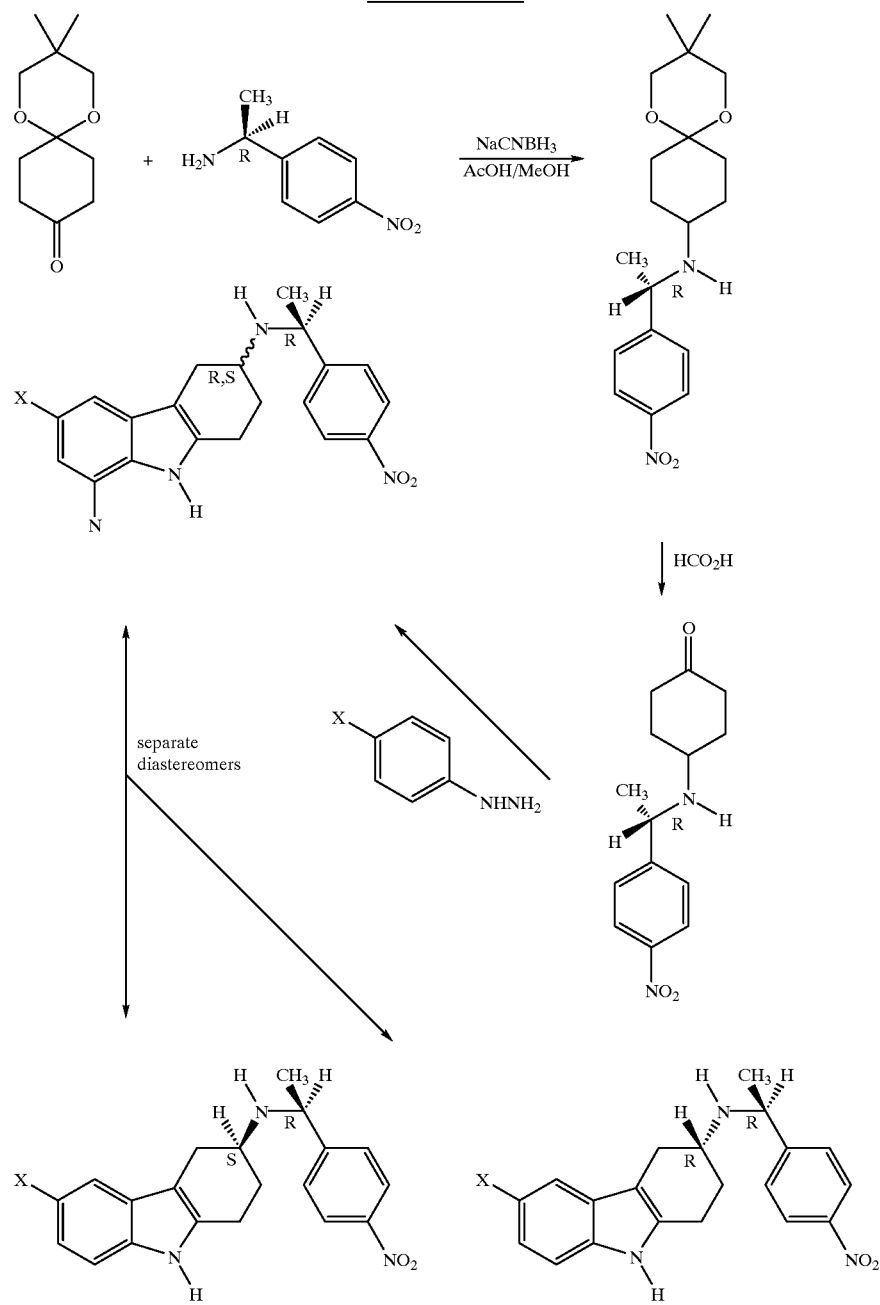

Synthetic Scheme X 1,4-cyclohexanedione mono-(2,2-dimethylpropane-1,3-diol)ketal is reductively aminated under standard conditions with an enantiomer of α-methyl-(4-nitrophenyl)ethylamine (Synthetic Scheme X illustrates the use of the R-(+)-enantiomer). The ketal is removed as described previously and the resulting aminocyclohexanone is subjected to the reaction conditions described for Synthetic Scheme I to give a diastereomeric mixture. The diastereomers are then separated by chromatography or fractional crystallization. The amine may then be treated, if desired, with an appropriate alkylating agent, for example an appropriate alkyl halide, to prepare the corresponding quaternary salt prior to cleavage of the α-methyl-(4-nitrophenyl)ethyl moiety.

Cleavage of the a-methyl-(4-nitrophenyl)ethyl moiety is achieved by reduction of the 4-nitro group followed by acid catalyzed solvolysis of the resulting α-methyl-(4-aminophenyl)ethyl moiety. Reduction of the nitro group can be accomplished by a wide range of reducing agents including, for example, titanium tetrachloride, lithium aluminum hydride, or zinc/acetic acid, or by catalytic hydrogenation. Solvolytic cleavage takes place when the monohydrochloride (or other monobasic salt) of the reduction product is treated with water or an alcohol at room temperature or, in some instances, at elevated temperatures. A particularly convenient condition for removing the α-methyl-(4-nitrophenyl)ethyl moiety is hydrogenation of the amine monohydrochloride in methanol over a sulfided platinum catalyst.

The reactions as illustrated in Synthetic Schemes VI–X are for the compounds of the invention which are either carbazoles or 10H-cyclohepta[7,6-b]indoles. The skilled artisan, however, will appreciate that the chemistry illustrated is applicable to either class of compounds. The skilled artisan will also appreciate that the order in which the steps are performed to prepare the compounds of the present invention are not important in many cases.

PREPARATION I 6-bromo-3-dimethylamino-9-triisopropylsilyl-1,2,3,4-tetrahydro-9H-carbazole 4-dimethylaminocyclohexanone (2,2-dimethylpropane-1,3-diol)ketal To a solution of 25.0 gm (554.6 mMol) dimethylamine in 500 mL methanol were added 50.0 gm (252.2 mMol) 1,4-cyclohexanedione mono-2,2-dimethylpropane-1,3-diol ketal and the reaction mixture was allowed to stir for 2 hours at room temperature. To this solution were then gradually added 31.69 gm (504.3 mMol) sodium cyanoborohydride. Once this addition was complete, acetic acid was added to adjust the mixture to a pH of about 6. The pH was monitored periodically and acetic acid additions continued to maintain the pH at about 6. When the addition of acetic acid no longer resulted in gas evolution, the reaction mixture was allowed to stir at room temperature for 18 hours. The reaction mixture was then concentrated under reduced pressure to a volume of about 100 mL and was then partitioned between 1N sodium hydroxide and dichloromethane. The remaining aqueous phase was treated with saturated aqueous sodium chloride and was again extracted with dichloromethane. These organic phases were combined, dried over sodium sulfate and concentrated under reduced pressure to give 40.15 gm (70%) of the desired compound as a yellow oil.

MS(m/e): 228(M+1).

4-dimethylaminocyclohexanone

A solution of 18.4 gm (81 mMol) 4-dimethylaminocyclohexanone (2,2-dimethylpropane-1,3-diol)ketal in 250 ML 90% formic acid were heated at reflux for 3 hours. The reaction mixture was then stirred at room temperature for 3 days. The reaction mixture was then diluted with 250 mL water and was concentrated to a volume of about 250 mL on a rotary evaporator. The dilution/concentration sequence was then repeated two more times. The residue was then further concentrated to a volume of about 50 mL, made basic with 5 N sodium hydroxide and extracted with dichloromethane. The organic phases were combined, dried over sodium sulfate and concentrated under reduced pressure to give 11.8 gm (100%) of the desired compound as a yellow oil.

MS(m/e): 141 (M$^+$); NMR(CDCl$_3$): δ 2.50 (m, 2H), 2.28 (m, 2H), 2.28 (m, 6H), 2.01 (m, 2H), 1.80 (m, 2H).

4-dimethylaminocyclohexanone 4-bromophenylhydrazone

To a mixture of 6.0 gm (42.0 mMol) 4-dimethylaminocyclohexanone and 9.5 gm (42.0 mMol) 4-bromophenyl-hydrazine hydrochloride in 100 mL ethanol were added 3.4 mL (42 mMol) pyridine. The resultant mixture was then heated at reflux for 2 hours and then stirred at ambient temperature for 18 hours. The reaction mixture was then treated with aqueous potassium carbonate and extracted well with dichloromethane. The organic phases were combined, dried over sodium sulfate and concentrated under reduced pressure. The resultant residue was treated with toluene and concentrated again under reduced pressure to give 11.3 gm (87%) of the desired compound.

6-bromo-3-(dimethyl)amino-1,2,3,4-tetrahydro-9H-carbazole hydrochloride

A solution of 11.3 gm (36.4 mMol) 4-dimethylaminocyclohexanone 4-bromophenylhydrazone in 250 mL 4M ethanolic hydrogen chloride were heated to reflux under nitrogen for 3 hours. The reaction mixture was allowed to cool to room temperature and was then concentrated under reduced pressure. The residual paste was dissolved in 200 mL water and to this solution were then added 50 mL 6 M hydrochloric acid. The mixture was cooled to 0° C. for 18 hours. The desired product which had crystallized was filtered and dried to give 8.66 gm (72%).

Silylation 8.66 gm (26.2 mMol) 6-bromo-3-dimethylamino-1,2,3,4-tetrahydro-9H-carbazole hydrochloride were partitioned between 1N sodium hydroxide and dichloromethane. The organic phase was dried over sodium sulfate and concentrated under reduced pressure. The residue was dissolved in 50 mL tetrahydrofuran and the resultant solution was added to a suspension of 8.0 gm (40 mMol) potassium hydride (20% in mineral oil) in 100 mL tetrahydrofuran cooled to about 0° C. The resultant mixture was stirred for an hour at this temperature and then to it were added 8.0 mL (30 mMol) triisopropylsilyltriflate and the mixture was allowed to warm gradually to room temperature. After 18 hours the reaction mixture was treated with ice to decompose excess potassium hydride. Once all of the hydride had been destroyed, the reaction mixture was diluted with 200 mL of water and was then extracted well with dichloromethane. The organic phases were combined, dried over sodium sulfate and concentrated under reduced pressure. The residual oil was subjected to silica gel chromatography, eluting sequentially with toluene, 9:1 toluene:ethyl acetate, 4:1 toluene:ethyl acetate, 1:1 toluene:ethyl acetate, and ethyl acetate. The ethyl acetate fractions were combined and concentrated under reduced pressure to give 7.08 gm (60%) of the title compound as a solid.

m.p.=92–93° C.; NMR(CDCl$_3$): δ 7.52 (d, 1H), 7.39 (dd, 1H), 7.13 (d, 1H), 3.04 (br dd, 1H), 2.88 (m, 2H), 2.70 (m, 1H), 2.58 (dd, 1H), 2.41 (s, 6H), 2.20 (d, 1H), 1.78 (m, 3H), 1.70 (m, 1H), 1.14 (m, 18H).

PREPARATION II

6-carboxy-3-dimethylamino-9-triisopropylsilyl-1,2,3,4-tetrahydro-9H-carbazole To a solution of 2.95 gm (6.56 mMol) 6-bromo-3-dimethylamino-9-triisopropylsilyl-1,2,3,4-tetrahydro-9H-carbazole in 150 mL tetrahydrofuran at −78° C. were added 16.4 mL (26.24 mMol) t-butyllithium (1.6 M in pentane). The dark solution was allowed to stir at this temperature for 1 hour and then carbon dioxide gas was bubbled through the solution until the dark color discharged to light yellow. After allowing the reaction mixture to warm to room temperature it was poured into water, the pH adjusted to about 7, and the mixture extracted well with dichloromethane. The organic phases were combined, dried over magnesium sulfate and concentrated under reduced pressure. The residue was triturated with hexane to give 2.31 gm (85%) of the desired compound as a tan foam.

IR: 3022, 2958, 2871, 1465, 1249 cm$^{-1}$; MS(m/e): 414 (M$^+$).

PREPARATION III

4-(1-phthalimidyl)cycloheptanone

To a stirred solution of 5.00 gm (20.55 mMol) 4-(1-phthalimidyl)cyclohexanone in 30 mL diethyl ether were added 3.79 mL (30.8 mMol) boron trifluoride ethereate. After stirring for 20 minutes at room temperature, 3.24 mL (30.8 mmol) ethyl diazoacetate were added dropwise. The resultant solution was stirred for 16 hours at room temperature. The reaction mixture was diluted with saturated aqueous sodium carbonate and was then extracted with diethyl ether. The combined organic extracts were dried over sodium sulfate and concentrated under reduced pressure. The residue was dissolved in 15 mL dimethylsulfoxide. To this solution were added 1.3 mL water and 1.5 gm sodium chloride. The resulting mixture was heated at 170° C. for 7 hours. The reaction mixture was then cooled, poured into 153 mL water and extracted well with diethyl ether. The combined organic phases were washed sequentially with water and saturated aqueous sodium chloride, dried over sodium sulfate and concentrated under reduced pressure. The residue was subjected to silica gel chromatography, eluting with 6:4 hexane:ethyl acetate. Fractions shown to contain product were combined and concentrated under reduced pressure to give 4.17 gm (79%) of the title compound.

MS(m/e): 257(M$^+$).

PREPARATION IV

(R)- and (S)-3-(N-α-methyl-4-nitrobenzyl)amino-6-bromo-2-amino-1,2,3,4-tetrahydro-9H-carbazole Reductive Amination To a solution of 20.0 gm (100.9 mMol) 1,4-cyclohexanedione mono-(2,2-dimethyl)propane-1,3-diol monoketal in 250 mL methanol were added 35.0 gm (172.7 mMol) R-(+)-α-methyl-4-nitrobenzylamine hydrochloride, 25.0 gm (398 mMol) sodium cyanoborohydride and 10 mL acetic acid. The reaction mixture was allowed to stir for 18 hours at room temperature. To the reaction mixture were then added an additional charge of 25.0 gm (398 mMol) sodium cyanoborohydride and the reaction mixture stirred for an additional 18 hours at room temperature. The reaction mixture was then diluted with dilute aqueous tartaric acid and the solution exhaustively extracted with dichloromethane. The remainining aqueous phase was made basic with aqueous sodium hydroxide and extracted well with dichloromethane. These dichloromethane extracts were combined, dried over sodium sulfate and concentrated under reduced pressure to give 33.7 gm (96%) of (R)-4-(N-α-methyl-4-nitrobenzyl)-aminocyclohexanone 2,2-dimethylpropane-1,2-diol ketal as a brownish yellow oil.

MS(m/e): 348(M$^+$).

Ketal Deprotection

A solution of 33.42 gm (95.91 mMol) (R)-4-(N-α-methyl-4-nitrobenzyl)aminocyclohexanone 2,2-dimethyl-propane-1,2-diol ketal in 250 mL 98% formic acid was heated to 40° C. for 66 hours. The reaction mixture was concentrated under reduced pressure to a volume of about 50 mL and was then treated with aqueous potassium carbonate. The basic aqueous mixture was extracted well with dichloromethane. These organic phases were combined, dried over sodium sulfate and concentrated under reduced pressure to give 22.36 gm (89%) (R)-4-(N-α-methyl-4-nitrobenzyl) aminocyclohexanone as a brown oil.

Preparation of Phenylhydrazone

To a solution of 22.3 gm (85.01 mMol) (R)-4-(N-α-methyl-4-nitrobenzyl)aminocyclohexanone in 375 mL ethanol were added 19.0 gm (85.0 mMol) 4-bromophenylhydrazine hydrochloride and 6.73 gm (85.1 mmol) pyridine. The reaction mixture was heated to 80° C. for 48 hours. The reaction mixture was cooled to room temperature and concentrated under reduced pressure. The residue was dissolved in dichloromethane and the organic solution was washed sequentially with aqueous potassium carbonate and saturated aqueous sodium chloride. The remaining organics were dried over sodium sulfate and concentrated under reduced pressure to give 31.66 gm (86%) (R)-4-(N-α-methyl-4-nitrobenzyl)aminocyclohexanone 4-bromophenyl-hydrazone as a brown solid.

Fischer Indole Reaction

A solution of 31.66 gm (73.4 mMol) (R)-4-(N-α-methyl-4-nitrobenzyl)aminocyclohexanone 4-bromophenyl-hydrazone in 500 mL 3.7 M ethanolic hydrogen chloride was stirred at reflux for 18 hours. The reaction mixture was cooled to room temperature and was then concentrated under reduced pressure. The residue was partitioned between 1 N sodium hydroxide and dichloromethane. The aqueous phase was extracted well with dichloromethane. The organic phases were combined, dried over sodium sulfate and concentrated under reduced pressure. The residue was subjected to silica gel chromatography, eluting with 5% methanol in dichloromethane which contained 1% ammonium hydroxide.

(3S)-(−)-3-(N-((R)-α-methyl-4-nitrobenzyl)amino)-6-bromo-1,2,3,4-tetrahydro-9H-carbazole The faster eluting diastereomer was recovered as 9.47 gm (31%) of a reddish-brown oil.

MS(m/e): 415(M$^+$); IR(CHCl$_3$): 3471, 2970, 2926, 2845, 1522, 1471, 1348, 857 cm$^{-1}$; [α]$_D^{20}$(c=10, methanol): −122.3°; Calculated for C$_{20}$H$_{20}$N$_3$O$_2$Br: Theory: C, 57.78; H, 4.87; N, 10.14. Found: C, 58.23; H, 5.03; N, 10.12.

(3R)-(+)-3-(N-((R)-α-methyl-4-nitrobenzyl)amino)-6-bromo-1,2,3,4-tetrahydro-9H-carbazole The slower eluting diastereomer was recovered as 8.13 gm (27%) of pale green crystals.

MS(m/e): 415(M$^+$); IR(CHCl$_3$): 3471, 3012, 2970, 2952, 2846, 1522, 1471, 1348, 857 cm$^{-1}$; [α]$_D^{20}$(c=10, methanol): +337.9°; Calculated for C$_{20}$H$_{20}$N$_3$O$_2$Br: Theory: C, 57.78; H, 4.87; N, 10.14. Found: C, 58.26; H, 5.03; N, 9.93; X-Ray crystallography determined that the slower eluting diastereomer was of the specified absolute configuration.

PREPARATION V

(R)-(+)-6-bromo-3-dimethylamino-1,2,3,4-tetrahydro-9H-carbazole hydroiodide

Quaternization

To a solution of 5.00 gm (12.1 mMol) (3R)-(+)-3-(N-((R)-α-methyl-4-nitrobenzyl)amino)-6-bromo-1,2,3,4-tetrahydro-9H-carbazole in 150 mL acetonitrile were added 10.0 mL iodomethane followed by 5.0 gm potassium carbonate. The mixture was stirred for 2 days at room temperature and then for 18 hours at reflux. The reaction mixture was then cooled to room temperature and the resulting yellow precipitate filtered, washed with methanol and dried under reduced pressure to give 3.65 gm (53%) (R)-(+)-3-(N,N-dimethyl-N-((R)-(+)-α-methyl-(4-nitrobenzyl)amino)-6-bromo-1,2,3,4-tetrahydro-9H-carbazole iodide as a yellow solid.

Calculated for $C_{22}H_{25}N_3O_2BrI$: Theory: C, 46.34; H, 4.42; N, 7.37. Found: C, 46.22; H, 4.41; N, 7.30.

Hydrogenolysis

A mixture of 0.70 gm (1.23 mMol) (R)-(+)-3-(N,N-dimethyl-N-((R)-(+)-α-methyl-(4-nitrobenzyl)amino)-6-bromo-1,2,3,4-tetrahydro-9H-carbazole iodide and 0.20 gm sulfided platinum on carbon in 150 mL methanol were hydrogenated at room temperature for 18 hours at an initial hydrogen pressure of 40 p.s.i. The reaction mixture was then degassed and warmed to effect methanolysis. The reaction mixture was filtered and concentrated under reduced pressure to give 0.471 gm (91%) of the title compound as a light yellow solid.

m.p.=252° C.; MS(m/e): 293(M$^+$); IR(KBr): 3271, 3016, 2924, 2842, 2737, 2709, 1469, 1460, 1435, 1308, 793 cm$^{-1}$; $[\alpha]_D^{20}$(c=10, methanol): +54.7°; Calculated for $C_{14}H_{18}N_2BrI$: Theory: C, 39.93; H, 4.31; N, 6.65. Found: C, 39.87; H, 4.19; N, 6.38.

PREPARATION VI

Resolution of Racemic 6-bromo-3-dimethylamino-1,2,3,4-tetrahydro-9H-carbazole To a solution of 5.0 gm (17.06 mMol) 6-bromo-3-dimethylamino-1,2,3,4-tetrahydro-9H-carbazole in 200 mL of warm ethyl acetate was added a solution of 6.59 gm (17.06 mMol) di-p-toluoyl-D-tartaric acid in 100 mL ethyl acetate with mixing. After standing for 4 hours, the resulting precipitate was filtered and dried to give 12.0 gm of the salt. A suspension of 1.0 gm of this solid was heated to boiling in 10 mL of methanol. This mixture was then cooled to room temperature and allowed to stand for 18 hours. The remaining solid was filtered and dried to give 0.65 gm. This solid was again suspended in 10 mL boiling methanol and allowed to cool and stand for 18 hours to give 0.52 gm of solid after filtration and vacuum drying. This solid was partitioned between dichloromethane and dilute aqueous sodium hydroxide. The phases were separated and the organics were washed with saturated aqueous sodium chloride, dried over sodium sulfate and concentrated under reduced pressure. The residue was dissolved in 7 mL of toluene and allowed to stand at room temperature for 18 hours. The solution was filtered to remove the solid which had formed and the filtrate was concentrated under reduced pressure to give 0.133 gm of an oil which gradually crystallized.

m.p.=131–3° C.; $[\alpha]_D^{20}$(c=10, methanol): –83°.

The two methanol filtrates were combined and concentrated under reduced pressure to give 0.33 gm of a glass. The glass was treated as described above to give 0.121 gm of an oil which gradually crystallized.

m.p.=131–4° C.; $[\alpha]_D^{20}$(c=10, methanol): +78°.

EXAMPLE 1

N-(pyridin-4-yl)-3-dimethylamino-1,2,3,4-tetrahydro-9H-carbazole-6-carboxamide Dihydrochloride A mixture of 0.41 gm (1.0 mMol) 3-dimethylamino-9-triisopropylsilyl-1,2,3,4-tetrahydro-9H-carbazole-6-carboxylic acid, 0.77 gm (4.0 mMol) 1-(3-dimethylaminopropyl)-3-ethylcarbodiimide hydrochloride, 0.54 gm (4.0 mMol) 1-hydroxybenzotriazole, and 0.38 gm (4.0 mMol) 4-aminopyridine in 10 mL dimethylformamide and 50 mL tetrahydrofuran were stirred together at room temperature for 3 days. Polystyrene bound isocyanate resin was added to the reaction mixture which was stirred at 40° C. for 6 hours to scavenge excess 4-aminopyridine. The reaction mixture was filtered, concentrated under reduced pressure and the residue subjected to preparative centrifugal thin layer chromatography (PCTLC), eluting with chloroform containing 5% methanol and 0.5% ammonium hydroxide. Fractions containing the desilylated product were combined and concentrated under reduced pressure to provide a yellow oil. This oil was dissolved in dichloromethane and treated with ethanolic hydrogen chloride. The resulting mixture was concentrated under reduced pressure to provide 0.22 gm (54%) of the title compound as a tan solid.

MS(m/e): 293(M$^+$); Calculated for $C_{20}H_{22}N_4O\cdot2HCl$: Theory: C, 58.97; H, 5.94; N, 13.75. Found: C, 58.77; H, 5.91; N, 13.79.

EXAMPLE 2

S-(–)-N-(pyridin-4-yl)-3-dimethylamino-1,2,3,4-tetrahydro-9H-carbazole-6-carboxamide Dihydrochloride Hemihydrate A mixture of 0.336 gm (0.81 mMol) S-(–)-3-dimethylamino-9-trimethylsilyl-1,2,3,4-tetrahydro-9H-carbazole-6-carboxylic acid, 0.171 gm (0.89 mMol) of 1-(3-dimethylaminopropyl)-3-ethylcarbodiimide hydrochloride, and 0.084 gm (0.89 mmol) 4-aminopyridine in 15 mL dimethylformamide was stirred at room temperature for 3 days. The reaction mixture was diluted with dichloromethane and then washed with water. The organic phase was dried over sodium sulfate and then concentrated under reduced pressure. The residue was subjected to silica gel chromatography as described in Example 1 to give 0.244 gm of partially desilylated product. The desilylation was completed by mixing with 5 mL tetrabutylammonium fluoride (1.0M in tetrahydrofuran) in 25 ml tetrahydrofuran containing 5 mL boric acid and stirring at room temperature for 18 hours. The reaction mixture was concentrated under reduced pressure and was then dissolved in aqueous tartaric acid and the resulting solution was washed well with dichloromethane. The remaining aqueous solution was made basic with 5N sodium hydroxide and then was extracted well with 10% isopropanol in chloroform. These organic phases were combined, dried over potassium carbonate, and concentrated under reduced pressure. The residue was subjected to PCTLC, eluting with chloroform containing 5% methanol and 0.5% ammonium hydroxide. Fractions containing product were combined and concentrated under reduced pressure. The residue was dissolved in chloroform containing methanol, and the solution placed on aVARIAN BOND ELUT SCX™ ion exchange column (Varian, Harbor City, Calif., U.S.A.). The column was washed with two volumes of methanol and then the column was eluted with 2N ammonia in methanol. Fractions containing product were combined and concentrated under reduced pressure. The residue was dissolved in ethanolic hydrogen chloride and the solution concentrated under reduced pressure to provide 0.044 gm (18%) of the title compound as a beige solid.

Calculated for $C_{20}H_{22}N_4O \cdot 2HCl \cdot 0.5H_2O$: Theory: C, 57.70; H, 6.05; N, 13.46. Found: C, 57.75; H, 5.84; N, 12.83.

General Procedure for the Coupling of Amines with 3-dimethylamino-1,2,3,4-tetrahydro-9H-carbazole-6-carboxylic Acids To a suspension of 4–5 equivalents of polymer bound 1-ethyl-3-(3-dimethylaminopropyl)carbodiimide (Desai, et al., *Tetrahedron Letters*, 34(48), 7685 (1993)) in chloroform are added 1 equivalent of 3-dimethylamino-1,2,3,4-tetrahydro-9H-carbazole-6-carboxylic acid and 2–3 equivalents of the appropriate amine. The reaction is agitated until the reaction is complete, heat may be applied if necessary. The resin is removed by filtration and the product isolated by evaporation of solvent. This procedure is illustrated by Examples 3–7.

EXAMPLE 3

N-cyclopropyl-3-(dimethyl)amino-1,2,3,4-tetrahydro-9H-carbazole-6-carboxamide

Beginning with 7.4 mg (0.029 mMol) 3-dimethylamino-1,2,3,4-tetrahydro-9H-carbazole-6-carboxylic acid and cyclopropylamine, 3.5 mg (41%) of the title compound were recovered.

MS(m/e): 298(M$^+$).

EXAMPLE 4

N-cyclopentyl-3-dimethylamino-1,2,3,4-tetrahydro-9H-carbazole-6-carboxamide

Beginning with 7.4 mg (0.029 mMol) 3-dimethylamino-1,2,3,4-tetrahydro-9H-carbazole-6-carboxylic acid and cyclopentylamine, 4.1 mg (41%) of the title compound were recovered.

MS(m/e): 342(M$^+$).

EXAMPLE 5

N-(5-methoxycarbonylfur-2-yl)-3-dimethylamino-1,2,3,4-tetrahydro-9H-carbazole-6-carboxamide Beginning with 7.4 mg (0.029 mMol) 3-dimethylamino-1,2,3,4-tetrahydro-9H-carbazole-6-carboxylic acid and 2-amino-5-methoxycarbonylfuran, 1.3 mg (10%) of the title compound were recovered.

MS(m/e): 370(M$^+$).

EXAMPLE 6

N-(2-chloropyridin-3-yl)-3-dimethylamino-1,2,3,4-tetrahydro-9H-carbazole-6-carboxamide Beginning with 7.4 mg (0.029 mMol) 3-dimethylamino-1,2,3,4-tetrahydro-9H-carbazole-6-carboxylic acid and 2-chloro-3-aminopyridine, 1.2 mg (9%) of the title compound were recovered.

MS(m/e): 369(M$^+$).

EXAMPLE 7

N-(6-methoxypyridin-3-yl)-3-dimethylamino-1,2,3,4-tetrahydro-9H-carbazole-6-carboxamide Beginning with 7.4 mg (0.029 mMol) 3-dimethylamino-1,2,3,4-tetrahydro-9H-carbazole-6-carboxylic acid and 6-methoxy-3-aminopyridine, 1.8 mg (14%) of the title compound were recovered.

MS(m/e): 365(M$^+$).

EXAMPLE 8

N-(pyridin-3-yl)-3- and -4-dimethylamino-10H-cyclohepta[7,6-b]indole-7-carboxamides 7-carboxy-3- and 4-(dimethylamino)cyclohepta[7,6-b]indole Hydrochloride A suspension of 1.40 gm (7.33 mMol) 4-(dimethylamino)cycloheptanone and 1.115 gm (7.33 mMol) 4-carboxyphenylhydrazine in 20.0 mL 5N hydrochloric acid was heated to reflux for 15 hour. The reaction mixture was then concentrated under reduced pressure to provide the title compound as a black solid.

MS(m/e): 272(M$^+$).

To a stirred solution of 0.541 gm (1.75 mMol) of a mixture of 3- and 4-dimethylamino-10H-cyclohepta[7,6-b]indole-7-carboxylic acid hydrochloride in 10 mL dimethylformamide are added 0.387 gm (2.38 mMol) carbonyldiimidazole. The reaction mixture is stirred for 15 minutes at room temperature and then 3.48 mMol 3-aminopyridine are added. The reaction mixture is stirred at room temperature for 20 hours, diluted with water and extracted with ethyl acetate. The organic phases are combined, washed well with water followed by saturated aqueous sodium chloride, and concentrated under reduced pressure. The residue is subjected to silica gel chromatography, eluting with chloroform containing 15% methanol and 1% ammonium hydroxide. Fractions containing the isomeric amines are combined and concentrated under reduced pressure to provide the title compounds.

The discovery that the 5-HT$_{1F}$ receptor mediates neurogenic meningeal extravasation, thereby causing the pain associated with migraine and associated disorders, is disclosed in U.S. Pat. No. 5,521,196, herein incorporated by reference in its entirety. To demonstrate the use of the compounds of this invention in the treatment of migraine, their ability to bind to the 5-HT$_{1F}$ receptor subtype was determined. The ability of the compounds of this invention to bind to the 5-HT$_{1F}$ receptor subtype was measured essentially as described in N. Adham, et al., *Proceedings of the National Academy of Sciences (USA)*, 90, 408–412 (1993).

Membrane Preparation: Membranes were prepared from transfected Ltk-cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA., pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding: [$^3$H-5-HT] binding was performed using slight modifications of the 5-HT$_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 μL of buffer (50 mM Tris, 10 mM MgCl$_2$, 0.2 mM EDTA, 10 μM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 6–12 concentrations of compound. Incubation times were 30 minutes for both saturation and displacement studies based upon initial investigations which determined equilibrium binding conditions. Nonspecific binding was defined in the presence of 10 μM 5-HT. Binding was initiated by the addition of 50 μL membrane homogenates (10–20 μg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). IC$_{50}$ values were converted to K$_i$ values using the Cheng-Prusoff equation (*Biochem. Pharmacol.*, 22, 3099–3108 (1973). All experiments were performed in triplicate. Representative compounds of this invention were found to have affinity for the 5-HT$_{1F}$ receptor as measured by the procedure described supra.

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Adenylate cyclase activity was determined using standard techniques. A maximal effect is achieved by serotonin. An E$_{max}$ is determined by dividing the inhibition of a test compound by the maximal effect and determining a percent inhibition. (N. Adham, et al., supra,; R. L. Weinshank, et al., *Proceedings of the National Academy of Sciences (USA)*, 89,3630–3634 (1992)), and the references cited therein.

Measurement of cAMP Formation

Transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 μM pargyline for 20 minutes at 37° C., 5% CO$_2$. Drug dose-effect curves were then conducted by adding 6 different final concentrations of drug, followed immediately by the addition of forskolin (10 μM). Subsequently, the cells were incubated for an additional 10 minutes at 37° C., 5% CO$_2$. The medium was aspirated and the reaction was stopped by the addition of 100 mM HCl. To demonstrate competitive antagonism, a dose-response curve for 5-HT was measured in parallel, using a fixed dose of methiothepin (0.32 μM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. Representative compounds of the invention were tested and found to be agonists at the 5-HT$_{1F}$ receptor in the cAMP assay.

Protein Extravasation Harlan Sprague-Dawley rats (225–325 g) or guinea pigs from Charles River Laboratories (225–325 g) are anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes are drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes (Rhodes Medical Systems, Inc.) are lowered through the holes in both hemispheres to a depth of 9 mm (rats) or 10.5 mm (guinea pigs) from dura.

The femoral vein is exposed and a dose of the test compound injected intravenously (1 mL/kg). Approximately 7 minutes later, a 50 mg/kg dose of Evans Blue, a fluorescent dye, is also injected intravenously. The Evans Blue complexes with proteins in the blood and functioned as a marker for protein extravasation. Exactly 10 minutes post-injection of the test compound, the left trigeminal ganglion is stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals are killed and exsanguinated with 20 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope (Zeiss) equipped with a grating monochromator and a spectrophotometer is used to quantify the amount of Evans Blue dye in each sample. An excitation wavelength of approximately 535 nm is utilized and the emission intensity at 600 nm is determined. The microscope is equipped with a motorized stage and also interfaced with a personal computer. This facilitates the computer-controlled movement of the stage with fluorescence measurements at 25 points (500 pm steps) on each dural sample. The mean and standard deviation of the measurements are determined by the computer.

The extravasation induced by the electrical stimulation of the trigeminal ganglion is an ipsilateral effect (i.e. occurs only on the side of the dura in which the trigeminal ganglion is stimulated). This allows the other (unstimulated) half of the dura to be used as a control. The ratio of the amount of extravasation in the dura from the stimulated side compared to the unstimulated side dura is calculated. Saline controls yield a ratio of approximately 2.0 in rats and 1.8 in guinea pigs. In contrast, a compound which effectively prevents the extravasation in the dura from the stimulated side would have a ratio of approximately 1.0. A dose-response curve is generated and the dose that inhibited the extravasation by 50% (ID$_{50}$) is approximated.

Sumatriptan, a commercially available treatment for migraine, exhibits low bio-availability and relatively short duration of action. Its affinity for a number of serotonin receptor subtypes gives rise to undesirable side effects, particularly vasoconstriction, which severely limits its utility in the treatment of migraine. Since compounds of this invention are potent agonists of the 5-HT$_{1F}$ receptor, extremely low doses are required to maintain therapeutic levels. Additionally, since compounds which are selective for the 5-HT$_{1F}$ receptor relative to other receptors do not cause vasoconstriction, complications due to vasoconstriction are avoided. Compounds of this invention also inhibit protein extravasation if administered prior or subsequent to stimulation of the trigeminal ganglia, suggesting they may be administered prior to an incipient migraine attack to prevent pain, or during a migraine attack to alleviate pain.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.a., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| Compound of Example 1 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Compound of Example 2 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Compound of Example 3 | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Compound of Example 5 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Compound of Example 6 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Compound of Example 7 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Compound of Example 1 | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
| --- | --- |
| Compound of Example 2 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
| --- | --- |
| Compound of Example 3 | 250.0 mg |
| Isotonic saline | 1000 ml |

Formulation Example 10

A topical formulation may be prepared as follows:

| Ingredient | Quantity |
| --- | --- |
| Compound of Example 4 | 110 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
|---|---|
| Compound of Example 5 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

What is claimed is:

1. A compound of Formula I:

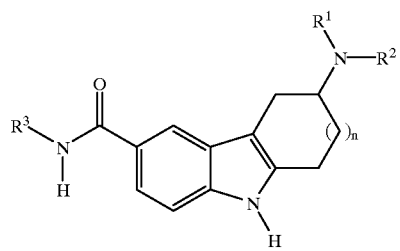

wherein:

$R^1$ and $R^2$ are independently hydrogen, $C_1$–$C_4$ alkyl, or —$CH_2CH_2$-Aryl where Aryl is phenyl, phenyl monosubstituted with halo, or 1-($C_1$–$C_6$ alkyl)pyrazol-4-yl;

$R^3$ is $C_3$–$C_6$ cycloalkyl or a heterocycle;

n is 1 or 2; or a pharmaceutically acceptable salt or hydrate thereof.

2. A compound of claim 1, where n is 1.

3. A compound of claim 2, where $R^1$ and $R^2$ are independently $C_1$–$C_4$ alkyl.

4. A pharmaceutical formulation which comprises, in association with a pharmaceutically acceptable carrier, diluent, or excipient, a compound of any of claims 1–3.

5. A method for the activation of 5-$HT_{1F}$ receptors in mammals, comprising administering to a mammal in need of such activation, an effective amount of a compound of any of claims 1–3.

6. A method for the inhibition of neuronal protein extravasation in mammals, comprising administering to a mammal in need of such inhibition, an effective amount of a compound of any of claims 1–3.

7. A method for the treatment of migraine, comprising administering to a mammal in need of such treatment, an effective amount of a compound of any of claims 1–3.

8. A method for the prevention of migraine in mammals, comprising administering to a mammal susceptible to migraine an effective amount of a compound of any of claims 1–3.

9. A method of claim 5 where the mammal is a human.

10. A method of claim 6 where the mammal is a human.

11. A method of claim 7 where the mammal is a human.

12. A method of claim 8 where the mammal is a human.

* * * * *